US008284402B2

(12) United States Patent
Frazier et al.

(10) Patent No.: US 8,284,402 B2
(45) Date of Patent: Oct. 9, 2012

(54) FLUORESCENCE DETECTION INSTRUMENT WITH ORTHOGONAL LASER ENTRY

(75) Inventors: Erich Frazier, Fort Lauderdale, FL (US); Helen A. Minnich, Fort Lauderdale, FL (US)

(73) Assignee: Beckman Coulter, Inc., Brea, CA (US)

( * ) Notice: Subject to any disclaimer, the term of this patent is extended or adjusted under 35 U.S.C. 154(b) by 147 days.

(21) Appl. No.: 12/713,881

(22) Filed: Feb. 26, 2010

(65) Prior Publication Data

US 2010/0220326 A1    Sep. 2, 2010

Related U.S. Application Data

(60) Provisional application No. 61/156,063, filed on Feb. 27, 2009.

(51) Int. Cl.
*G01N 21/25* (2006.01)

(52) U.S. Cl. ....................................................... 356/419

(58) Field of Classification Search .................. 356/419; 250/226; 385/36, 52
See application file for complete search history.

(56) References Cited

U.S. PATENT DOCUMENTS

| | | | |
|---|---|---|---|
| 4,244,045 A * | 1/1981 | Nosu et al. ....................... | 398/86 |
| 5,737,104 A | 4/1998 | Lee et al. | |
| 5,859,717 A | 1/1999 | Scobey et al. | |
| 6,042,249 A | 3/2000 | Spangenberg | |
| 6,084,994 A | 7/2000 | Li et al. | |
| 6,125,221 A | 9/2000 | Bergmann et al. | |

(Continued)

OTHER PUBLICATIONS

Lebo, Roger V. et al., "Design and Application of a Versatile Triple-Laser Cell and Chromosome Sorter," *Cytometry*, 8:71-82, 12 pages, 1987.

Steinkamp, John A. et al., "Improved multilaser/multiparameter flow cytometer for analysis and sorting of cells and particles," *Rev. Sci. Instrum.*, 62(11) 2751-2764, 14 pages, Nov. 1991.

(Continued)

*Primary Examiner* — Tarifur Chowdhury
*Assistant Examiner* — Abdullahi Nur
(74) *Attorney, Agent, or Firm* — K&L Gates LLP; Louis C. Cullman; Thomas A. Turano (57) ABSTRACT

A detector assembly for analysis of light emitted form a fluorescent material, an optical alignment assembly for introducing an output beam into a detector array or demultiplexer, and methods of demultiplexing a beam of light into wavelength bands. The detector assembly generally includes an optical alignment assembly to introduce an output beam having a projected optical axis into an array of filters. The optical alignment assembly is mounted substantially orthogonally to a plane of reflective light defined by the path of the output beam through the filter array. The array includes filters arranged in two rows in parallel. Each filter transmits a particular band of the output beam and reflects the remaining bands to the next filter in the opposite row of filters. The array further includes a plurality of detectors mounted in detector ports. The optical alignment assembly presented herein generally includes a housing configured to receive an optical fiber, at least one collimating lens, a rotatable housing member with a beam reflecting element attached thereto. The optical alignment assembly is adjustable to introduce an output beam into a detector array utilizing a rotational adjustment mechanism and a goniometric tilt adjustment mechanism. These two mechanisms ensure that the point of entry of a light beam into the array remains at a fixed point in space despite the rotation or tilt of the rotatable housing member.

26 Claims, 9 Drawing Sheets

U.S. PATENT DOCUMENTS

| | | | |
|---|---|---|---|
| 6,198,864 B1 | 3/2001 | Lemoff et al. | |
| 6,870,976 B2 | 3/2005 | Chen et al. | |
| 7,038,778 B2 * | 5/2006 | Yamauchi | 356/419 |
| 7,129,505 B2 | 10/2006 | Oostman, Jr. et al. | |
| 2002/0154428 A1 | 10/2002 | Nasu et al. | |
| 2007/0274364 A1 * | 11/2007 | Brown et al. | 372/71 |

OTHER PUBLICATIONS

International Search Report and the Written Opinion of the International Searching Authority, application No. PCT/US2010/25546, dated Apr. 16, 2010.

* cited by examiner

FLUORESCENCE DETECTION INSTRUMENT WITH ORTHOGONAL LASER ENTRY

CROSS-REFERENCE TO RELATED APPLICATIONS

This application is a non-provisional application claiming the benefit under 35 U.S.C. §119(e) of U.S. Provisional Application No. 61/156,063, filed on Feb. 27, 2009, which is incorporated herein by reference in its entirety.

BACKGROUND OF THE INVENTION

1. Field of the Invention

The present invention relates to systems and methods for fluorescence detection.

More specifically, the present invention relates to fluorescence detection assemblies for analysis of fluorescent signals from target substances.

2. Background

Flow cytometry is commonly used to differentiate various types of cells and other "formed bodies" comprising a biological fluid, e.g., whole blood. Conventional flow cytometers commonly comprise an optically-transparent flow cell, usually made of quartz, having a central channel through which a stream of cells to be individually identified is made to flow. Movement of the cell stream through the flow cell channel can be hydrodynamically entrained to the central longitudinal axis of the flow cell channel by a cell-free sheath liquid that concentrically surrounds the cell stream and flows along with the cell stream as it passes through the flow cell channel. As each cell passes through a cell-interrogation zone of the flow cell channel, it is irradiated with a focused beam of radiation (as commonly provided by a laser source). Upon impinging upon each cell, the laser beam is scattered in a pattern characteristic of the morphology, density, refractive index and size of the cell. Further, the spectral characteristics of the laser beam may act to excite certain fluorochromes associated with selected cells, as may be the case when a cell's DNA has been previously stained with such fluorochromes, or when a fluorochrome molecule has been previously conjugated with a selected type of cell, either directly or via an intermediate bead or the like. Photodetectors strategically positioned about the optical flow cell serve to convert the light scattered by each cell and the fluorescence emitted by the excited fluorochromes to electrical signals which, when suitably processed, serve to identify the irradiated cell. A conventional light scatter and fluorescence-sensing flow cytometer of the type noted above is disclosed in U.S. Pat. No. 7,392,908 to Frazier, the disclosure of which is incorporated herein by reference in its entirety.

As an alternative to positioning photodetectors directly about the optical flow cell, a light collector can be used to gather fluorescent light emitted by the excited fluorochromes. The light collector, which can be a group of lens elements, images the emitted light to a plurality of optical fibers. Each optical fiber transmits light to an array of photodetectors, which in turn convert the fluorescence emitted by the excited fluorochromes to electrical signals for analysis.

Various types of photodetector arrays have been used to separate light into discrete wavelengths to aid in fluorescence analysis. One such detector array is disclosed by "Improved Multilaser/Multiparameter Flow Cytometer for Analysis and Sorting of Cells and Particles," John A. Steinkamp et al., Review of Scientific Instruments, Vol. 62, No. 11, pp. 2751-2764, November 1992 ("the Steinkamp publication"). The Steinkamp publication describes a detector configuration that includes four dichroic filters to separate light into discrete wavelengths. The dichroic filters are arranged in one line, and each filter except the last in line reflects a certain band of light to an associated detector and transmits the remaining bands to the next detector. The last filter reflects one band of light to a detector and transmits the remaining wavelengths of light to a final detector.

A second type of detector array configuration is disclosed by U.S. Pat. No. 4,244,045 to Nosu et al. ("the Nosu patent"). Optical fibers introduce a beam of light into the demultiplexer, which is designed to separate light into multiple wavelengths. The demultiplexer includes six optical filters, each of which transmits certain wavelengths therethrough and reflects light waves with wavelengths sufficiently different from the transmitted wavelengths. Three optical filters are arranged on each side of an avenue. A light beam is introduced into the array via an optical fiber and a collimating rod lens positioned in parallel to the avenue at an angle of incidence of 15 degrees. The first optical filter, on the opposite side of the avenue from the collimating lens, receives light directly from the collimating lens. The next four optical filters receive light from a reflected beam coming from another of the optical filters located on the opposite side of the avenue.

Detector assemblies such as that described by the Steinkamp publication and the Nosu patent are generally prefabricated blocks. As a result, multiple detector assemblies must be used if it is desired to analyze multiple light beams, for example, light beams of different color spectrums. Another problem with known detector assemblies and demultiplexers is that the blocks must be prefabricated based on the number of wavelengths of light to be separated, i.e., each block is manufactured with space for a predetermined number of dichroic filters and detectors. As a result, these prefabricated detector assemblies are not customizable to accommodate multiple light beams, each of which may require separation of a different amount of wavelengths.

The present invention provides detector arrays that can be customized with regard to the number of optical inputs that can be analyzed in order to accommodate changing numbers of optical inputs. Such detector arrays can be adjusted such that the number of dichroic filters and detectors associated with each optical input can be adjusted in order to separate a light beam into more or fewer wavelengths without requiring multiple detector assemblies.

BRIEF SUMMARY OF THE INVENTION

The detector assemblies described herein seek to remedy one or more of the disadvantages of previous detector assemblies by providing assemblies that can be customized as to the number of optical inputs that can be analyzed and the number of dichroic filters and detectors associated with each optical input. The various detector assembly embodiments described herein can be used to analyze light emitted from a fluorescent material. Also provided herein are various embodiments of an optical alignment assembly for introducing an output beam into a detector array or demultiplexer. Various embodiments of methods of demultiplexing a beam of light into its component wavelength bands are also described herein. The presented detector assemblies generally include optical alignment assemblies to introduce an output beam having a projected optical axis into an array of filters. The optical alignment assemblies are mounted substantially orthogonally to a plane of reflective light defined by the path of the output beam through the filter array. The array includes filters arranged in two rows in parallel. The filters transmit a particular band of the output beam and reflect the remaining bands to the next filter in the opposite row of filters. The array further includes a plurality of detectors mounted in detector ports. The detectors receive the transmitted legs of the output beam. The presented methods include steps for using the presented detector arrays for demultiplexing a beam of light into its component wavelengths. The optical alignment assembly presented herein generally includes a housing configured to receive an optical fiber, at least one collimating lens, and a rotatable housing member with a beam reflecting element attached thereto. The optical alignment assembly is adjustable to introduce an output beam into a detector array utilizing a rotational adjustment mechanism and a goniometric tilt adjustment mechanism. These two mechanisms ensure that the point of entry of a light beam into the array remains at a fixed point in space despite the rotation or tilt of the rotatable housing member.

BRIEF DESCRIPTION OF THE FIGURES

The accompanying figures, which are incorporated herein, form part of the specification and illustrate embodiments of a detector assembly for analysis of light emitted form a fluorescent material. Together with the description, the figures further serve to explain the principles of and to enable a person skilled in the relevant art(s) to make and use the detector assembly and methods described herein. In the drawings, like reference numbers indicate identical or functionally similar elements.

DETAILED DESCRIPTION OF THE INVENTION

The following detailed description of detector assemblies and methods for demultiplexing a beam of light refers to the accompanying figures that illustrate exemplary embodiments. Other embodiments are possible. Modifications can be made to the embodiments described herein without departing from the spirit and scope of the present invention. Therefore, the following detailed description is not meant to be limiting. Further, it would be apparent to one of skill in the art that the systems and methods described below can be implemented in many different embodiments of hardware. Any actual hardware described is not meant to be limiting. The operation and behavior of the systems and methods presented are described with the understanding that modifications and variations of the embodiments are possible given the level of detail presented. For example, while the description provided incorporates the detector assembly into a flow cytometry system, the detector assembly and optical alignment assemblies and methods presented herein should not be limited to the field of flow cytometry. One of skill in the art would readily understand how to incorporate the presented detector assembly and demultiplexing methods into other native environments, such as, for example, blood analysis systems, cell sorting systems, DNA analysis systems, etc.

Figure 1:
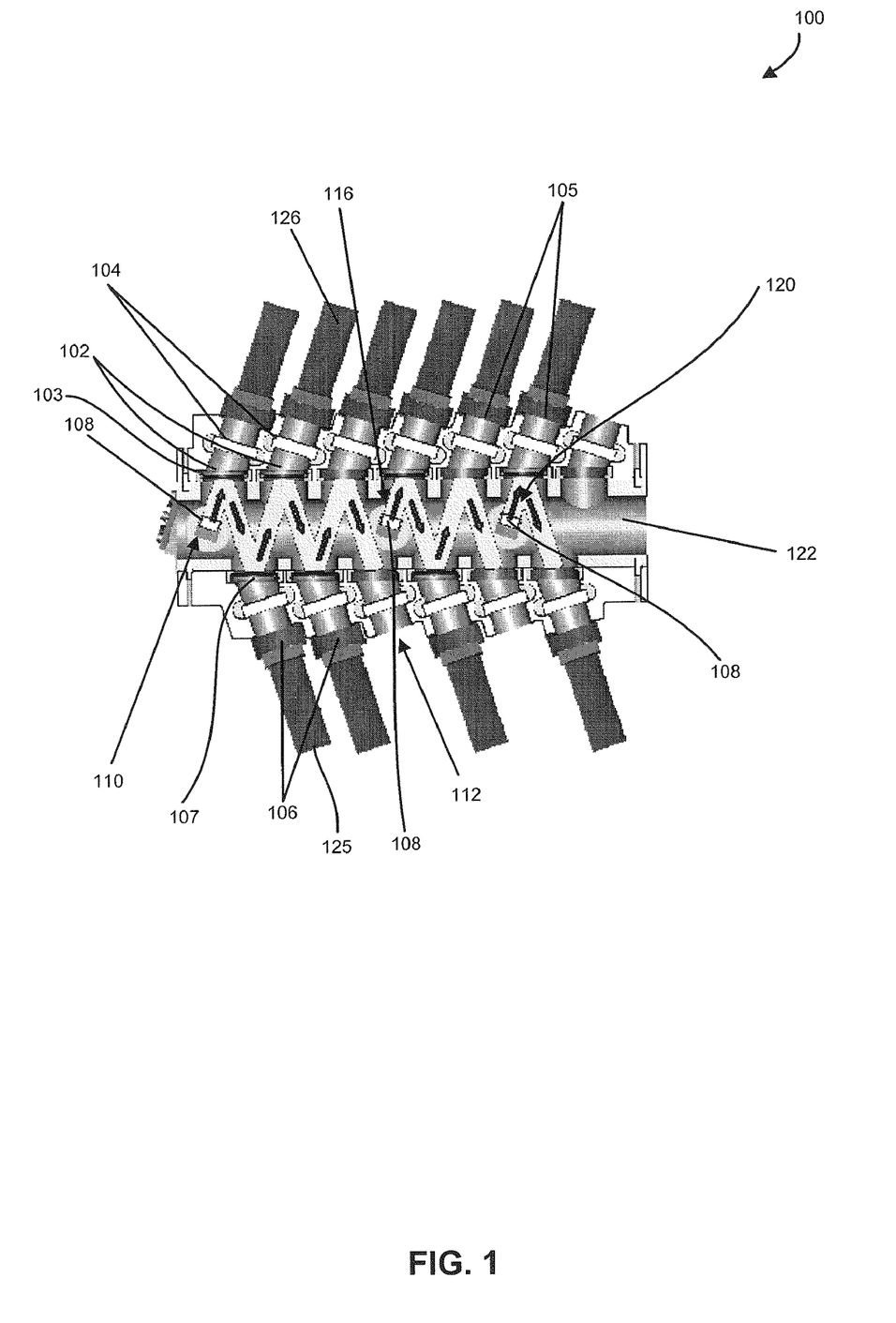
FIG. 1 is a cross-section view of a detector assembly in accordance with one embodiment presented herein.

FIG. 1 is a cross-section view of a detector assembly 100. In the embodiment presented, detector assembly 100 includes a plurality of dichroic filters 102, a plurality of bandpass filters 104, and a plurality of detectors 106 housed in detector ports 105. In one embodiment, detectors 106 are photomultiplier tubes (PMTs). It is understood that various other types of photodetectors, for example, photo avalanche detectors, can be used in embodiments of detector assembly 100. Light beams 110, 116, and 120 are introduced into a central boulevard 122 of the detector assembly by three optical alignment assemblies 400 (shown in FIGS. 3-7B), each of which includes a beam reflecting element 108. Optical alignment assemblies 400 are mounted substantially orthogonal to the central boulevard 122. Each optical alignment assembly includes a beam reflecting element 108, which is a minor, or, more preferably, a prism, that reflects a beam of light from the optical alignment assembly into the central boulevard 122. A prism has the advantage of providing total internal reflections, i.e., no reflective coating is required on the prism surface. A mirror generally requires a reflective coating, which is disadvantageous because of expense and manufacturing difficulties. Although detector assembly 100 is shown with three beam reflecting elements 108 corresponding to three optical alignment assemblies 400, detector assembly 100 can be adjusted to include more or fewer optical alignment assemblies according to the number of inputs to be analyzed. Specifically, embodiments of the detector assembly can include at least two optical alignment assemblies, four or more optical alignment assemblies, and even seven or more alignment assemblies. Because the optical alignment assemblies 400 are mounted orthogonally to the central boulevard 122, the number of optical alignment assemblies can be adjusted without altering the spacing of detector ports 105. In addition, although the detector assembly shown in FIG. 1 includes thirteen detector ports, embodiments of the detector assembly can include more or fewer detector ports as desired. As will be explained in further detail herein, the ability to customize the number of optical alignment assemblies, and the number of detectors associated with each optical alignment assembly, without requiring multiple detector assembly blocks provides multiple benefits over previous detector assemblies.

In operation, a first light beam 110 is reflected into the central boulevard 122 by a beam reflecting element 108. Light beam 110 travels in the indicated direction towards a first dichroic filter 103. Dichroic filter 103 splits light beam 110 such that a portion of the beam that falls within a particular band of optical signals is transmitted through the dichroic filter 103 while light in other bands is reflected towards a second dichroic filter 107. Although filters 102 are described herein as dichroic filters, it is understood that other types of filters, mirrors, or reflectors can be used in place of dichroic filters to pass a particular band of optical signals while reflecting remaining bands. Thus, as used herein, the term dichroic filter refers to any device that passes a particular band of optical signals while reflecting remaining bands. The transmitted portion of beam 110 then passes through a bandpass filter 104 and into a detector 106 for analysis. Bandpass filters 104 further isolate a desired band of wavelengths from the transmitted portion of beam 110. The reflected portion of beam 110 travels to dichroic filter 107, where a second band of optical signals is transmitted to a second detector while the remaining bands are reflected onward. Each dichroic filter 102 along the path of light beam 110 removes a selected band of light in the same manner, but with different wavelengths of light being separated. In the embodiment shown in FIG. 1, beam 110 encounters five dichroic filters 102 before the remaining band of optical signals passes into a detector port 112. Although the embodiment shown in FIG. 1 does not illustrate a detector in detector port 112, it is understood that a detector could be included in port 112 to receive any remaining bands of optical signals.

The embodiment shown in FIG. 1 illustrates a detector assembly 100 including three beam reflecting elements 108 corresponding to three optical alignment assemblies 400. Each beam reflecting element 108 introduces a light beam into the central boulevard 122, and each light beam reflects off one or more dichroic filters 102 before impinging upon a final detector housed in a detector port 105. As explained in further detail with reference to FIGS. 3-7B, beam reflecting elements 108 are preferably mirrors, or more preferably prisms, each of which is secured to an optical alignment assembly 400 mounted to the top of the detector assembly 100. The words top and bottom are used herein only as convenient relative terms for description purposes, and are not intended to limit what is referenced to any particular orientation relative to some absolute reference orientation. It is understood that alignment assemblies other than those shown in FIGS. 3-7B could be used to deliver a beam of light to beam reflecting elements 108. Preferably, the beam reflecting elements 108 are positioned such that the angle of incidence of the beam on the dichroic filters 102 is less than twenty degrees. More preferably, the angle of incidence is less than nineteen degrees, and most preferably less than eighteen degrees. Lower angles of incidence provide less polarization of light compared to higher angles.

In the embodiment illustrated in FIG. 1, a first beam 110 reflects off of five dichroic filters, a second beam 116 reflects off of three dichroic filters, and a third beam 120 reflects off of one dichroic filter. The number of dichroic filters encountered by each light beam is merely exemplary. Both the location and number of optical alignment assemblies can be adjusted such that less or more than three optical alignment assemblies are included in the detector assembly, and the number of dichroic filters 102 associated with the beam of light emitted from each optical alignment assembly can be increased or decreased without reconfiguring the position of the detector ports 105 along central boulevard 122. In a preferred embodiment, the detector assembly 100 includes thirteen detector ports. Alternately, detector assembly 100 can be provided with any number of detector ports, with the number limited only by the physical size of the detector assembly 100.

Figure 2:
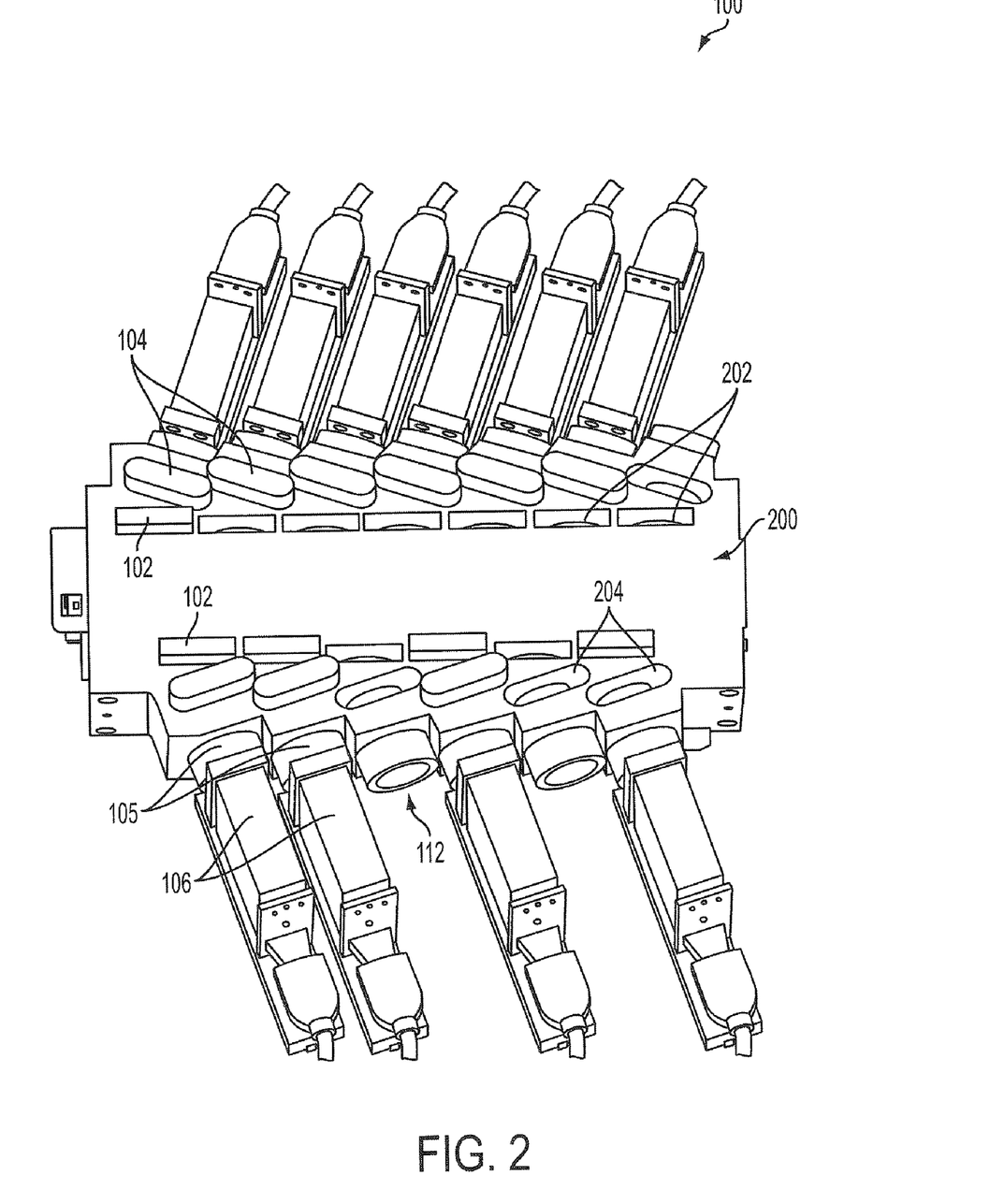
FIG. 2 is a bottom view of a detector assembly in accordance with one embodiment presented herein.

FIG. 2 is a view of the bottom 200 of a detector assembly in accordance with one embodiment presented herein. As shown in FIG. 2, detector assembly 100 is formed with a plurality of dichroic filter slots 202 therein. Dichroic filter slots 202 are formed in two rows in parallel. The slots 202 in each row are evenly spaced, and, depending on the desired configuration of the detector assembly 100, may or may not have dichroic filters 102 inserted therein. Each dichroic filter slot 202 has a bandpass filter slot 204 associated therewith. The bandpass filter slots 204 are formed at an angle to the dichroic filter slots 202, and the slots 204 in each row are evenly spaced. A detector port 105 is located behind each bandpass filter slot 204, and a detector 106 can be mounted in each detector port 105. Dichroic filters 102, bandpass filters 104, and detectors 106 can be added or removed from the detector assembly 100 as necessary for a desired application.

Figure 3:
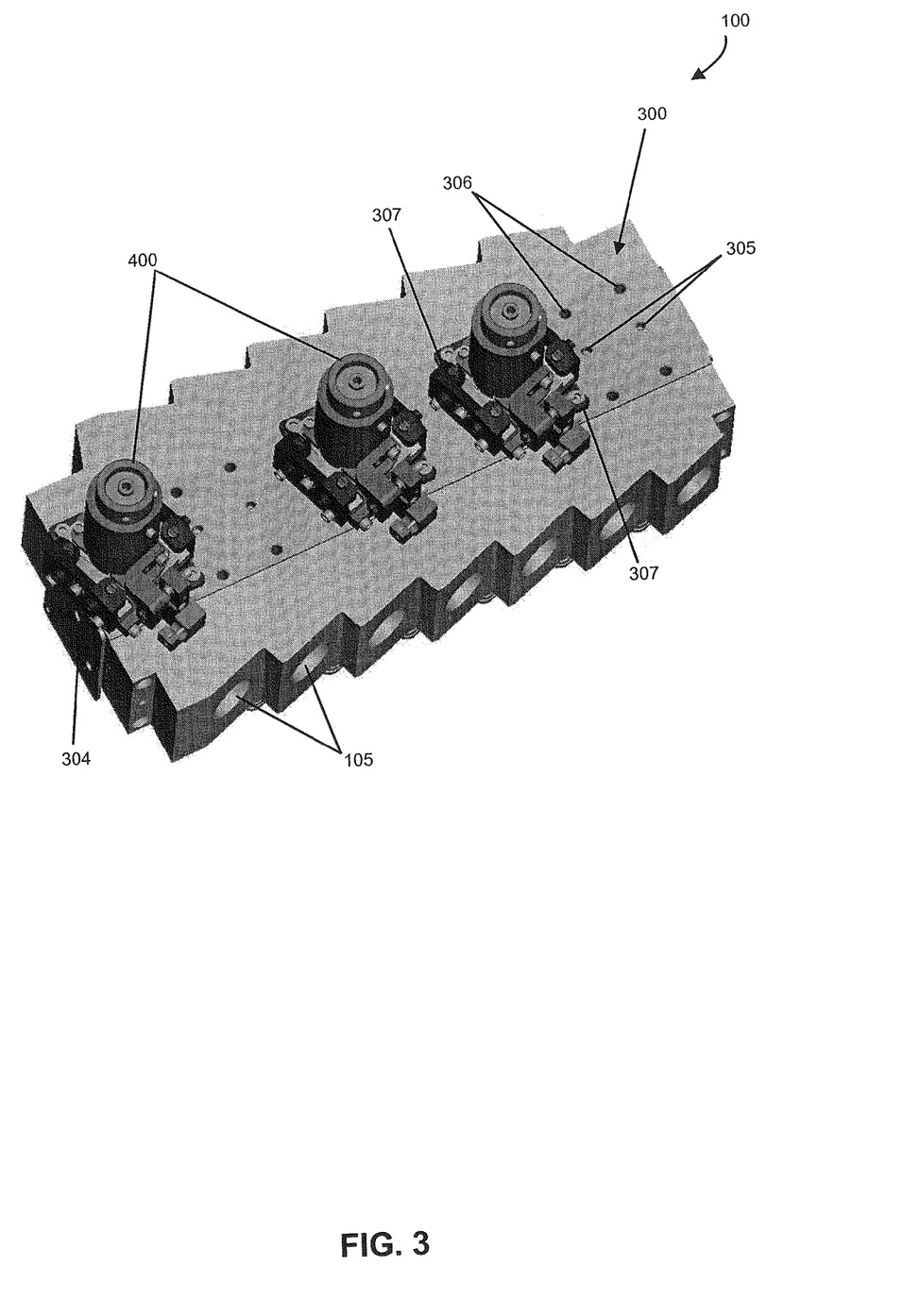
FIG. 3 is a perspective view of the top of a detector assembly in accordance with one embodiment presented herein including three optical alignment assemblies.
Figure 6A:
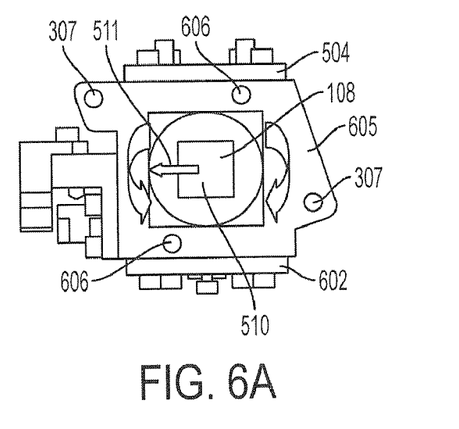
FIGS. 6A-6C are bottom views of the optical alignment assembly shown in FIG. 4.

FIG. 3 is a perspective view of the top of a detector assembly 100 in accordance with one embodiment presented herein. Detector assembly 100 includes three optical alignment assemblies 400, which are mounted on the top surface 300 of detector assembly 100. An endcap 304 is attached to each end of the detector assembly in order to enclose central boulevard 122. Top surface 300 of detector assembly 100 is provided with a plurality of threaded mounting holes 306 and a plurality of unthreaded mounting holes 305. Each detector assembly is also provided with a plurality of screw receiving holes 307 on a bottom support plate 605 of the assembly. As shown in FIG. 6A, mounting pins 606 are also positioned on bottom support plate 605 of optical alignment assembly 400 in order to assist in positioning the optical alignment assembly 400 on the top surface 300 of detector assembly 100. Optical alignment assemblies 400 are mounted to the detector assembly by aligning mounting pins 606 with unthreaded mounting holes 305 and securing the optical alignment assemblies to the detector assembly 100 using mounting screws that pass through screw receiving holes 307 and are secured in threaded mounting holes 306.

Although various fastening members are described herein, it is understood that a wide variety of devices and methods can be used to fasten optical alignment assemblies 400 to detector assembly 100, and to attach the components of the optical alignment assemblies to each other. For example, bolts, pins, tongue and groove arrangements, brackets, or even welding can be used instead of screws, or in addition thereto, to fasten any of the various components of detector assemblies 100 and optical alignment assemblies 400 together. Any reference herein to a particular fastening method is merely exemplary.

By arranging the optical alignment assemblies 400 in the above described manner such that a light beam enters the detector assembly 100 orthogonally to a plane defined by the path of the output beam through the detector array allows the number of optical alignment assemblies to be increased or decreased on location by an end user of the detector assembly without sacrificing one or more detector positions. As noted above in the Background of the Invention section, detector arrays are generally prefabricated blocks. As a result, multiple detector assembly blocks had to be used to analyze multiple light beams, for example, light beams of different color spectrums. In addition, prior art detector assemblies were not easily scalable and could not be easily adapted on location to accommodate advances in fluorescence detection. Specifically, prior art detector assemblies could not be modified to include additional detectors once the detector assembly block was delivered to an end user. In order to split a beam of light into more bands than the detector assembly block was initially configured for, an entirely new detector assembly would have to be ordered. In contrast, the detector assemblies described herein allow for rapid adjustment of the number of detectors associated with a particular optical alignment assembly.

In previous detector arrays utlizing a boulevard arrangement, light was introduced into the array via a mechanism arranged in parallel to a plane defined by the path of the output beam through the detector array. Because of this parallel arrangement, even if one was inclined to include multiple optical alignment assemblies in a single pre-manufactured detector assembly block, the block would have an unnecessarily large footprint. It would also be impossible to increase the number of detectors associated with each optical alignment assembly. Specifically, as shown in FIGS. 1-3, orthogonal entry into the central boulevard 122 allows for a detector assembly block to be used with multiple optical alignment assemblies while simultaneously preserving even spacing between dichroic filters 102. This provides multiple benefits. For example, with reference to FIGS. 1 and 2, light beam 110 terminates at detector port 112. However, because the dichroic filter slots 202 and their corresponding detectors 106 are arranged in evenly spaced rows around the central boulevard 122, the number of dichroic filters associated with the first light beam 110 can be increased by removing the second optical alignment system from the assembly and including an additional dichroic filter in the dichroic filter slot associated with detector port 112. In this manner, light beam 110 can be filtered into additional wavelengths without the need for a new detector assembly block.

Similarly, detector assembly 100 can be reconfigured to include additional optical alignment assemblies, with the understanding that at least one wavelength range is separated from the light beam before the light beam reaches its final detector. For example, with reference to FIG. 1, light beam 110 could terminate at detector 125 and a fourth light beam could be introduced into the detector assembly 100 at a point between detector 125 and detector 126. Furthermore, a detector assembly as described herein could be provided with any number of detector ports in order to accommodate further expansion of both the number of optical alignment assemblies 400 included in the detector assembly 100 as well as the number of detectors associated with each light beam introduced into the filter array. Such customization was not possible with prior art detector assemblies.

Arranging an optical alignment assembly in parallel to the central boulevard, as disclosed by the prior art, requires a significant amount of space. Even if one attempted to extend the detector arrays of the prior art in order to accommodate multiple optical alignment assemblies, the dichroic filters and corresponding detector ports would not be evenly spaced. This is because, at the entry point of a second light beam, a large space between detector ports would be needed to accommodate a second optical alignment assembly. Because of this space, an end user would be limited to the number of light beam entry points provided in the pre-fabricated detector assembly block, and would not be able to add additional light beam entry points to the assembly. Furthermore, the end user would not have the ability to increase the number of detector ports associated with a particular light beam because of the space required between detectors to accommodate the optical alignment assemblies. As noted above with reference to FIG. 1, the number of dichroic filters associated with the first light beam 110 can be increased by removing the second optical alignment system from the assembly and including an additional dichroic filter in the dichroic filter slot associated with detector port 112. Because the detector ports are evenly spaced, the light beam would be aligned with the next detector port without the need for further adjustment to the assembly. In the hypothetical extended detector assembly using parallel entry, the light beam would not be aligned with the next detector port even if the second optical alignment assembly was removed.

Figure 4:
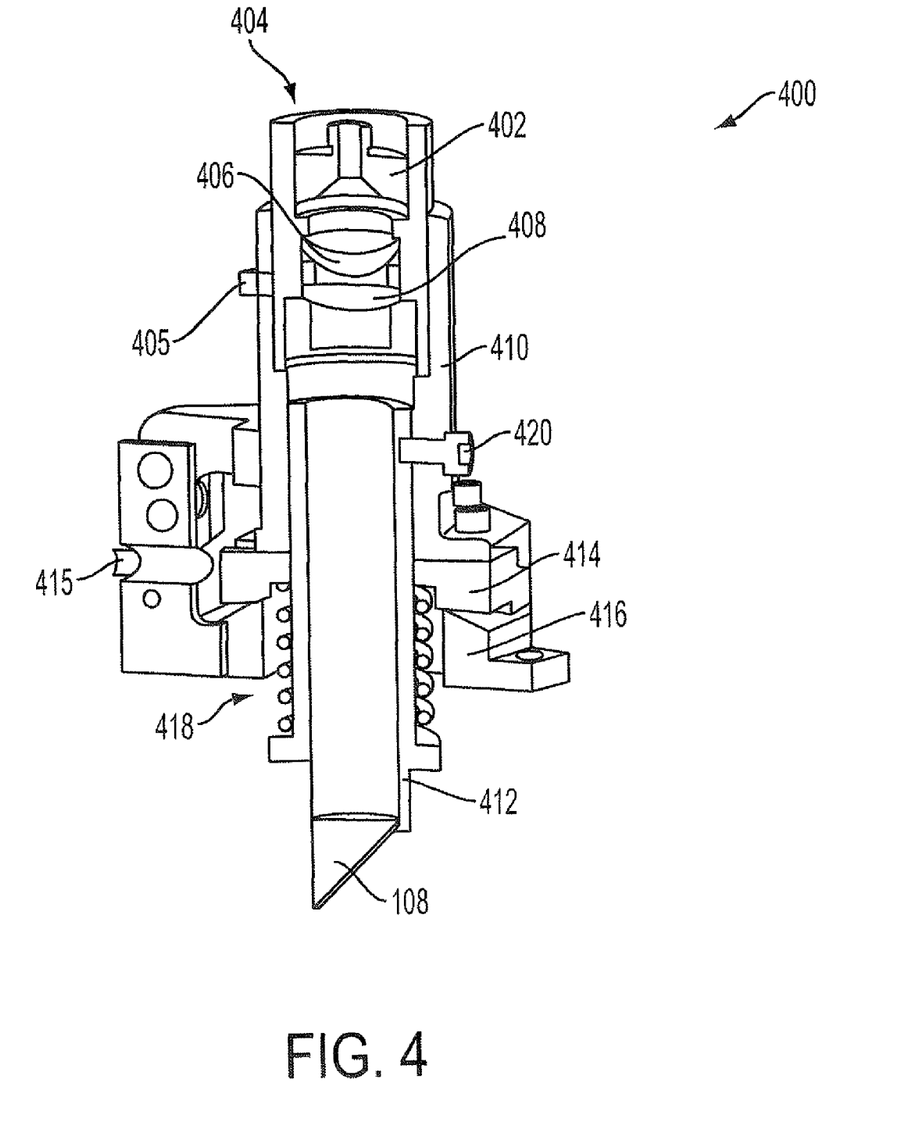
FIG. 4 is a cross-sectional view of an optical alignment assembly in accordance with one embodiment presented herein.

FIG. 4 is a cross-sectional view of an optical alignment assembly 400 in accordance with one embodiment presented herein. Optical alignment assembly 400 allows for rotational and goniometric movement that preserves the optical center of the start of the collimated beam, while allowing adjustments to maintain alignment with detectors 106 along the central boulevard 122. In the embodiment shown in FIG. 4, the tubular portion of the optical alignment assembly 400 includes a collimator housing 404, an upper barrel 410, and a lower barrel 412. It is understood that instead of being formed in a tubular or barrel shape, the collimator housing 404, including the upper barrel 410 and the lower barrel 412 portion could be formed in a variety of other shapes. An optical fiber port 402 with a focusing disk is provided to receive and an optical fiber and focus the light transmitted by the optical fiber. First and second collimator lenses 406 and 408 are secured in collimator housing 404. Although, in the present embodiment, two collimator lenses and a focusing disk are utilized to receive and focus light from the optical fiber, it is understood that alternate lens arrangements can be provided in collimator housing 404 to focus light received from the optical fiber. Collimator housing 404 is secured to upper barrel 410, preferably by a screw 405. Upper barrel 410 is secured to lower barrel 412, preferably by a screw 420. A beam reflecting element 108 is provided at the bottom of the lower barrel 412. As described herein with reference to FIG. 1, the beam reflecting element 108 reflects a collimated beam of light from the first and second collimator lenses 406 and 408 such that the beam of light emitted from the optical alignment assembly 400 travels along the central boulevard 122. Spring 418 biases the beam reflecting element 108 away from upper barrel 410. Although spring 418 is depicted as a coil spring, it is understood that other elements, such as a gasket, could be used to provide a biasing force to bias reflecting element 108 away from upper barrel 410.

Optical alignment assembly 400 further includes a slidable base 414 and a fixed base 416. In at least one embodiment, slidable base 414 and fixed base 416 are curved such that the concave curvature of the bottom surface of slidable base 414 generally matches the convex curvature of the top surface of fixed base 416. In operation, the position of slidable base 414 in relation to fixed base 416 can be adjusted in order to align the output beam with the detectors 106 positioned along the central boulevard 122. This adjustment is accomplished by manipulation of a tilt screw 415 that applies pressure to one side of slidable base 414. A spring (not shown) biases the slidable base 414 towards the tilt screw 415. The spring is anchored at one end to the slidable base 414, and at the other end to a screw 708, shown in FIGS. 7A and 7B. Thus, in operation, the screw can be tightened in order to push the slidable base 414 away from the screw, while loosening the tilt screw 415 results in the slidable base 414 moving in the direction of the screw due to the biasing effect of the spring.

Figure 5A:
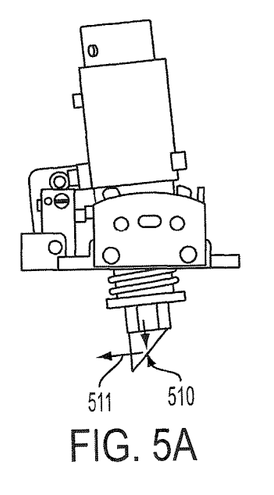
FIGS. 5A-5C are side views of the optical alignment assembly shown in FIG. 4.
Figure 5B:
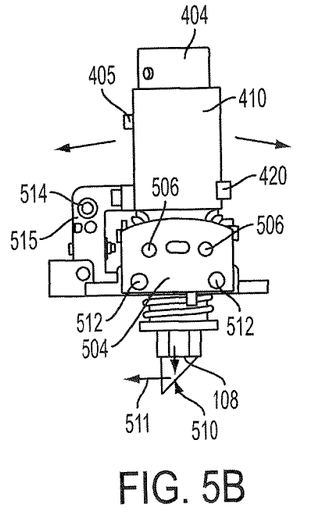
Figure 5C:
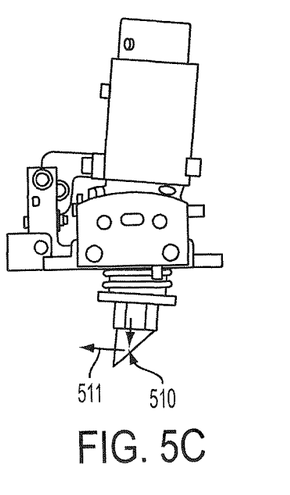

As shown in FIGS. 5A-5C, optical alignment assembly 400 allows adjustment of the output angle of a light beam 511 relative to the central boulevard 122. In a present embodiment, the curved surfaces of slidable base 414 and fixed base 416 allows the optical alignment assembly to function as a positioning goniometer such that manipulation of tilt screw 415 rotates the beam reflecting element 108 about a fixed axis in space. As a result of this goniometric motion, the point of entry 510 of a light beam 511 into the central boulevard 122 remains unchanged as the optical alignment assembly is tilted. Regardless of the direction or amount of tilt of the tubular portion of optical alignment assembly 400, the point of entry 510 remains at substantially the same point in three dimensional space. Light beam 511 therefore enters the central boulevard 122 from the same point no matter how much the mechanism is tilted, thus preserving alignment with the detectors arranged along the central boulevard 122.

Several other features of one embodiment are shown with reference to FIG. 5B. The optical alignment assembly 400 is provided with a left side plate 504. Mounting holes 512 are formed in left side plate 504 to assist in anchoring fixed base 416 thereto. Plungers 506 enable fine tuning of the position of slidable base 416, and an adjustment screw 514, coupled with a tensioning spring (not shown) provide further left to right adjustments of C-bracket 515, which is secured to the side of upper barrel 410 by locating pin 715 and fastening screw 714, which are shown in FIG. 7A.

Figure 6B:
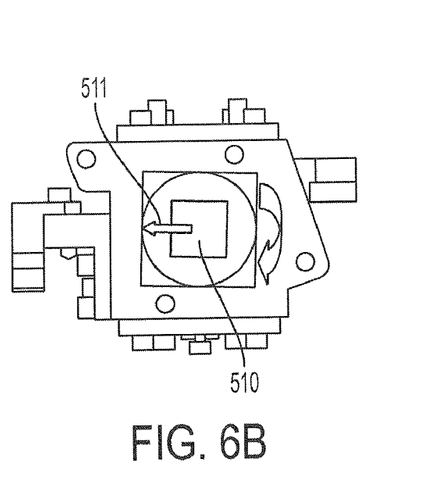
Figure 6C:
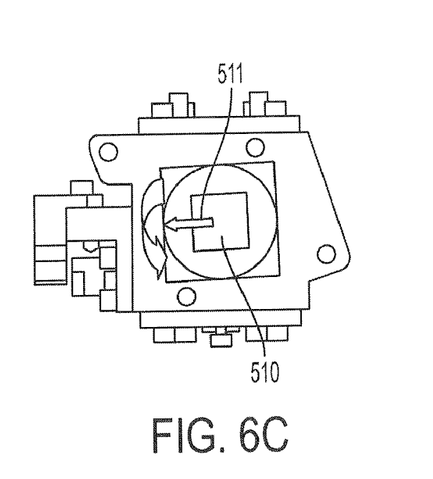

The rotational adjustment of optical alignment assembly 400, and more specifically the rotational adjustment of beam reflecting element 108, is described in further detail with reference to FIGS. 6A-6C. FIGS. 6A-6C are bottom views of optical alignment assembly 400, with arrows demonstrating the rotational adjustment. Rotational adjustment of the beam reflecting element 108 provides a second mechanism to direct light beam 511 into central boulevard 122 at a desired angle. Rotational adjustment of the beam reflecting element 108 is effectuated by manipulation of screw 514, shown in FIGS. 5B and 7A. As screw 514 is pushed against C-bracket 515, upper barrel 410 rotates in a clockwise direction causing beam reflecting element 108 to rotate in a clockwise direction. A spring (not shown) biases the C-bracket 515 towards the screw 514. Thus, as the screw is withdrawn, C-bracket 515 and beam reflecting element 108 rotate in a counterclockwise direction. As with the tilting adjustment mechanism described with reference to FIGS. 5A-5C, the rotational adjustment mechanism ensures that the point of entry 510 of light beam 511 into the central boulevard 122 remains at the same point in three dimensional space regardless of the direction or amount of rotation of beam reflecting element 108. By utilizing optical alignment assembly 400, only two adjustments (tilt adjustment and rotation adjustment) are necessary in order to align a light beam with the detectors 106 in central boulevard 122. The goniometric tilt adjustment and rotational adjustment also operate independently of each other. Traditional optical alignment systems typically required four adjustments, and the four adjustments were interdependent.

Figure 7A:
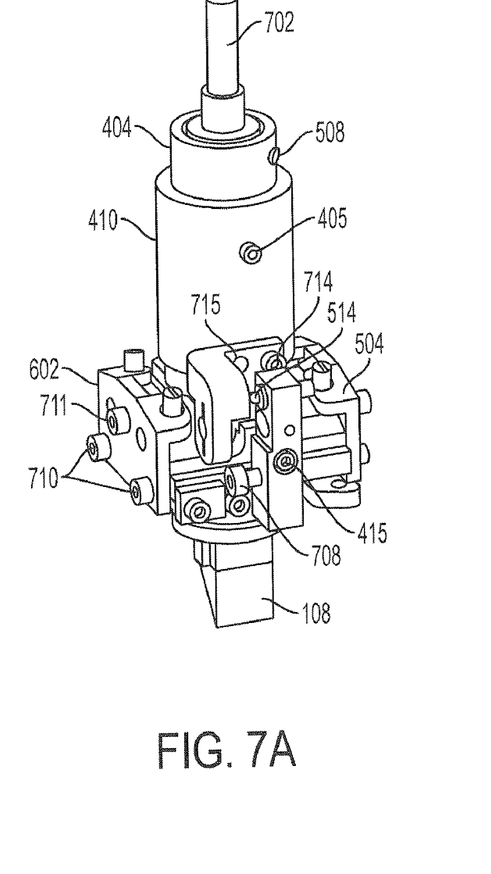
FIGS. 7A and 7B are additional side views of the optical alignment assembly shown in FIG. 4.
Figure 7B:
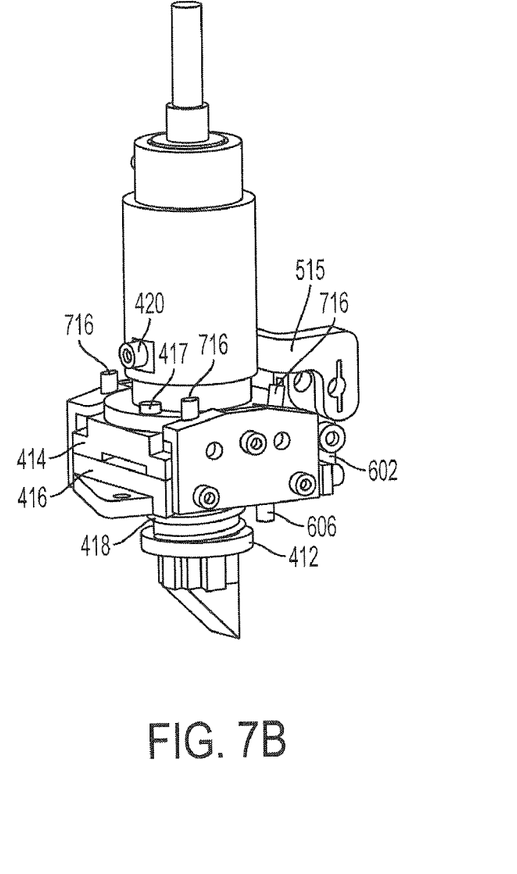

FIGS. 7A and 7B are additional side views of the optical alignment assembly shown in FIG. 4. When in use, an optical fiber 702 is inserted into the top of optical alignment assembly 400. The optical fiber 702 introduces a light beam into the optical alignment assembly 400. With reference to FIG. 4, once introduced into the optical alignment assembly, the light beam passes through a focusing disk 402, a first collimator lens 406, and a second collimating lens 408 before being reflected by a beam reflecting element 108 into the central boulevard 122.

In certain embodiments, left side plate 504 and right side plate 602 are identical. However, as explained with reference to FIG. 5B, two plungers 506 are inserted into the upper holes of left side plate 504 to enable fine tuning of the position of slidable base 416. Both left and right side plates 504 and 602 are provided with mounting screw holes 512. In one embodiment, mounting screws 710 are inserted into the mounting screw holes 512 of both left and right side plate 504 and 602 to secure fixed base 416 in position. A screw 711 is inserted into a center upper hole in right side plate 602 to secure slidable base 414 once it has been adjusted to the desired position. Rolling-ball tip set screws 716 are inserted through the top surface of left and right side plates 504 and 602 in order to further secure slidable base 414. The rolling-ball tip screws 716 secure slidable base 414 in the desired position without damaging the base, and without the need for specially designed screws to match the curvature of slidable base 414. However, in other embodiments, specially designed screws or standard tip screws could be used in place of rolling-ball tip set screws 716.

Figure 8:
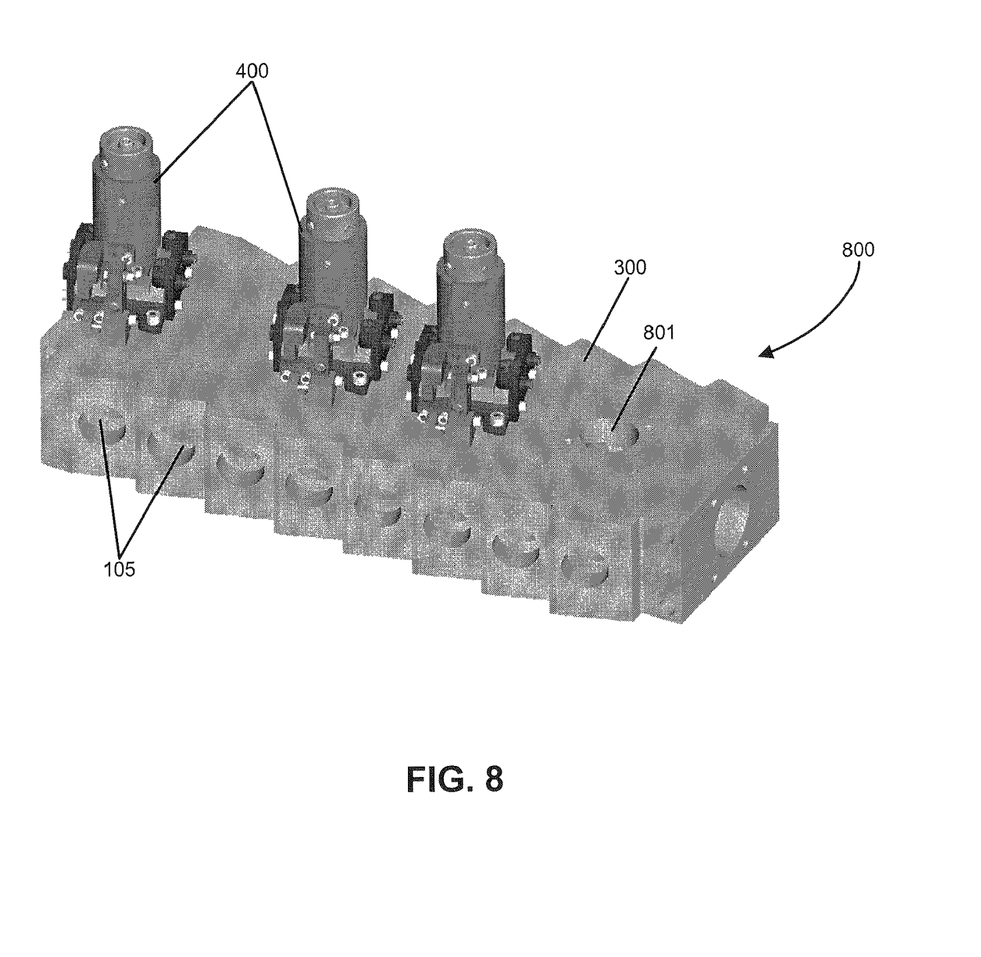
FIG. 8 is a perspective view of the top of a detector assembly in accordance with one embodiment presented herein having additional detector ports and optical alignment assembly mounting positions.
Figure 9:
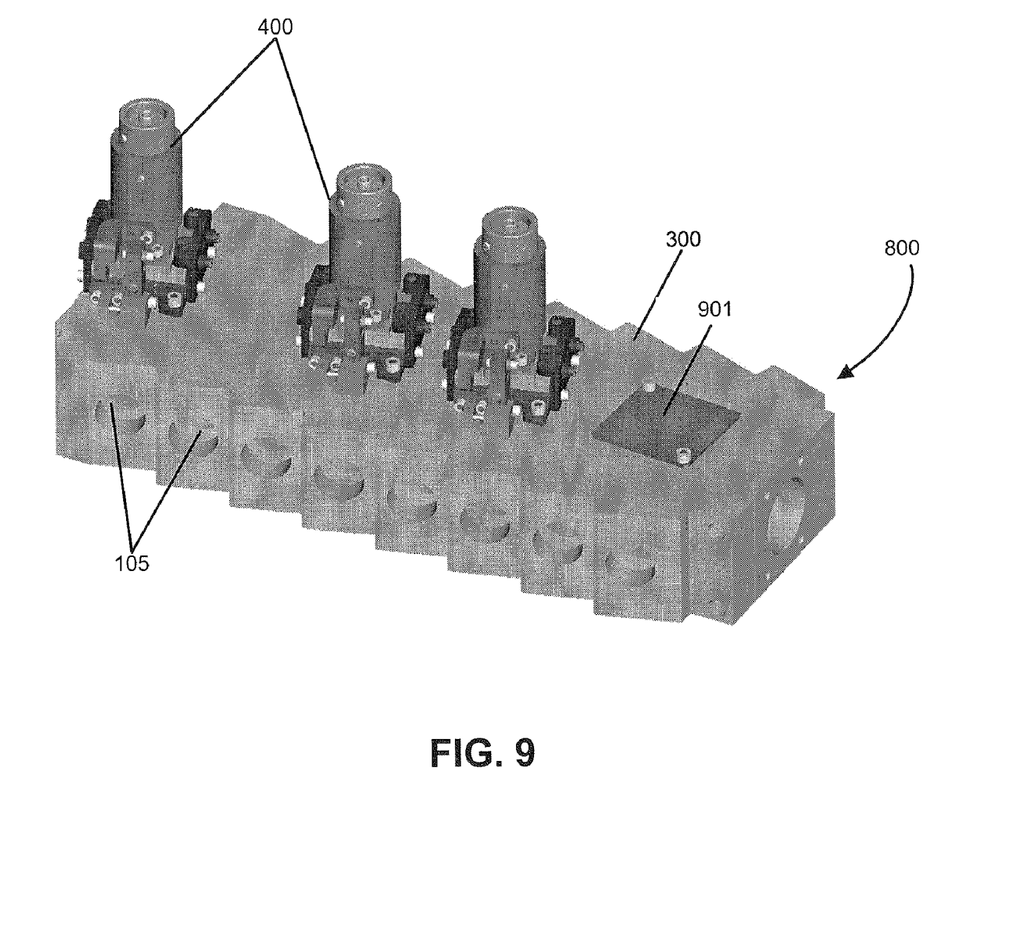
FIG. 9 is a perspective view of the top of a detector assembly in accordance with one embodiment presented herein including a cover plate for a through-hole opening in the top of the detector assembly.

FIG. 8 illustrates a detector assembly in accordance with another embodiment of the present invention. Detector assembly 800 includes sixteen detector ports 105. FIG. 8 also illustrates through-hole 801 formed in the top surface 300 of detector assembly 800, into which a fourth optical alignment assembly 400 can be mounted. Through-holes can also be provided, though are not illustrated, in the embodiments described above with reference to FIGS. 1-3. For example, detector assembly 100, as shown in FIG. 3, is provided with three through-holes into which the lower barrels 412 of optical alignment assemblies 400 are inserted. Both detector assemblies 100 and 800 can be provided with additional through-holes to accommodate additional optical alignment assemblies. For example, additional through-holes and corresponding optical alignment assemblies 400 can be provided between the first and second optical alignment assemblies in detector assemblies 100 and 800. Further, embodiments of detector assemblies according to the present invention can be longer than those shown in the Figures, and can accommodate more than sixteen detector ports 105 and more than four optical alignment assemblies 400. An optical alignment assembly can be mounted at the location of through-hole 801 in order to provide analysis of additional wavelengths of light. As shown in FIG. 9, a cover plate 901 can be used to cover any through-holes that are not used for a particular light analysis application. Such a cover ensures that no external light enters the central boulevard 122. In some applications, detector assemblies according to the present invention can be operated in a light-sealed enclosure, in which case there is no need for a cover plate 901 to cover open through-holes. In these applications, unused through-holes can remain open with no harm to the performance of the detector assembly.

EXAMPLES

The following paragraphs serve as examples of the above-described embodiments.

Example 1

One embodiment provides a detector assembly for analysis of light. The detector assembly comprises an optical alignment assembly configured to provide an output beam having a projected optical axis and a dichroic filter array having a plurality of dichroic filters arranged in two rows in parallel. Preferably, a majority of the dichroic filters are configured to receive light from another dichroic filter. The dichroic filters are located in slots, and each row of slots includes a plurality of evenly spaced slots. At least half of the dichroic filters split the output beam into a reflected leg and a transmitted leg. The reflected legs of the output beam preferably have a dichroic reflection angle of less than twenty degrees, more preferably less than nineteen degrees, and most preferably less than 18 degrees. The dichroic filters in each parallel row are evenly spaced from the other dichroic filters in their respective parallel row. The detector assembly further includes a plurality of detector ports for receiving detectors therein, wherein said detectors receive a transmitted leg of the output beam. The optical alignment assembly is mounted substantially orthogonally to a plane of reflective light defined by the path of the output beam. Each output beam is associated with one or more detectors that receive light from the output beam, and the number of detectors receiving light from an output beam can be increased without altering the number or position of the detectors. The optical alignment assembly comprises a housing configured to receive an optical fiber, a collimating lens configured to collimate a beam of light emitted by the optical fiber, a rotatable housing member, a beam reflecting element attached to the rotatable housing member, and an alignment system utilizing two adjustment mechanisms, wherein a first adjustment mechanism adjusts rotation of the rotatable housing member and a second adjustment mechanism adjusts the goniometric tilt of the rotatable housing member.

Alternately, two or more optical alignment assemblies, each mounted substantially orthogonally to the plane of reflective light, are included in the detector assembly of Example 1. Each optical alignment assembly is configured to provide a respective output beam having a projected optical axis.

Example 2

Another embodiment provides a detector assembly for analysis of light emitted from a fluorescent material. The detector assembly comprises a dichroic filter array having a plurality of dichroic filters arranged in two rows in parallel. The dichroic filters are located in slots, and each row of slots includes a plurality of evenly spaced slots. The dichroic filters are configured to split the output beam into a reflected leg and a transmitted leg. The detector assembly further includes a first optical alignment assembly configured to generate a first output beam having a first projected optical axis and a second optical alignment assembly configured to generate a second output beam having a second projected optical axis. The first and second optical alignment assemblies are mounted substantially orthogonally to a plane of reflective light defined by the path of the output beam. The first output beam enters the dichroic filter array at a first location and the second output beam enters the dichroic filter array at a second location. A plurality of detector ports for receiving detectors therein are also included in the detector assembly, wherein said detectors receive a transmitted leg of the output beams. At least the second optical alignment assembly is configured to be removed from or repositioned on the detector assembly. One or more detector ports are configured to receive light from the first output beam, and the detector assembly is configured such that the number of detector ports receiving light from the first output beam can be increased by removing one of the optical assemblies and adding a corresponding dichroic filter. The first and second optical alignment assemblies comprise a housing configured to receive an optical fiber, a collimating lens configured to collimate a beam of light emitted by the optical fiber, a rotatable housing member, a beam reflecting element attached to the rotatable housing member, and an alignment system utilizing two adjustment mechanisms, wherein a first adjustment mechanism adjusts rotation of the rotatable housing member and a second adjustment mechanism adjusts the goniometric tilt of the rotatable housing member.

The detector assembly may also include a third optical alignment assembly configured to generate a third output beam having a third projected optical axis, wherein the third output beam enters the dichroic filter array at a third location.

Example 3

In another embodiment providing an optical alignment assembly for introducing an output beam into an array of dichroic filters, the optical assembly comprises a housing configured to receive an optical fiber, a collimating lens configured to collimate a beam of light emitted by the optical fiber, a rotatable housing member, a beam reflecting element, such as a prism, attached to the rotatable housing member, and an alignment system utilizing two adjustment mechanisms, wherein a first adjustment mechanism adjusts rotation of the rotatable housing member and a second adjustment mechanism adjusts the goniometric tilt of the rotatable housing member. The beam reflecting element is configured to reflect the collimated beam into the array of dichroic filters, and the beam reflecting element reflects light at an angle of approximately 90 degrees. The beam reflecting element reflects light at a reflection point inside the beam reflecting element, and the position of the reflection point remains substantially the same as the tilt of the rotatable housing member is adjusted. The rotatable housing member has a barrel shape. The first adjustment mechanism is independent from the second adjustment mechanism, and the second adjustment mechanism comprises a first curved surface and a second curved surface, wherein the first curved surface abuts the second curved surface and is slidable in relation to the second curved surface. The optical alignment assembly further includes a spring configured to bias the beam reflecting element away from the second adjustment mechanism.

The optical alignment assembly may further include a second collimating lens. The optical assembly may further include a focusing disk or a lens configured to focus the light emitted by the optical fiber on the collimating lenses.

Example 4

In one example, detector assembly 100 is used for demultiplexing a beam of light, for example, a fluorescent pulse, transmitted by an optical fiber. The method for demultiplexing includes the following steps:
  a) collimating the beam of light with a collimating lens;
  b) redirecting the beam of light with a beam reflecting element, such as a prism, such that the beam of light enters a dichroic filter array having a plurality dichroic filters arranged in two rows in parallel, and goniometrically adjusting the angle at which the beam of light exits the beam reflecting element;
  c) separating the beam of light into its component wavelengths by reflecting the beam of light off at least one of the dichroic filters and reflecting the beam of light off two or more of the dichroic filters, wherein the beam of light is alternately reflected between a dichroic filter located in the first row and a dichroic filter in the second row; and
  d) filtering the beam of light with a bandpass filter, wherein the beam of light, prior to being redirected by the beam reflecting element, is approximately orthogonal to a plane of reflective light defined by the path of the beam after the beam is redirected by the beam reflecting element.

In step b), the beam of light is reflected off the at least one dichroic filter at an angle preferably less than about 20 degrees, more preferably less than about 19 degrees, and most preferably less than about 18 degrees.

The foregoing description of the invention has been presented for purposes of illustration and description. It is not intended to be exhaustive or to limit the invention to the precise form disclosed. Other modifications and variations may be possible in light of the above teachings. The embodiments and examples were chosen and described in order to best explain the principles of the invention and its practical application and to thereby enable others skilled in the art to best utilize the invention in various embodiments and various modifications as are suited to the particular use contemplated. It is intended that the appended claims be construed to include other alternative embodiments of the invention.

What is claimed is:

1. A detector assembly for analysis of light, the detector assembly comprising:
   an optical alignment assembly having a longitudinal axis and configured to provide an output beam having a projected optical axis;
   a dichroic filter array having a plurality of dichroic filters arranged in two rows in parallel; and
   a plurality of detector ports for receiving detectors therein, wherein said detectors receive a transmitted leg of the output beam,
   wherein the projected optical axis of the output light beam, when reflected between the rows of dichroic filters, lies in a plane, and
   wherein the optical alignment assembly is mounted with the longitudinal axis of the optical alignment assembly substantially orthogonal to the plane.

2. The detector assembly of claim 1 comprising two or more optical alignment assemblies each having a respective longitudinal axis mounted substantially orthogonally to the plane of reflective light, wherein each optical alignment assembly is configured to provide a respective output beam having a projected optical axis.

3. The detector assembly of claim 2, wherein the dichroic filters in each parallel row are evenly spaced from the other dichroic filters in their respective parallel row.

4. The detector assembly of claim 2, wherein each output beam is associated with one or more detectors that receive light from the output beam, and wherein the number of detectors receiving light from an output beam can be increased without altering the number or position of the detectors.

5. The detector assembly of claim 1, wherein at least half of the dichroic filters split the output beam into a reflected leg and a transmitted leg, and wherein the reflected legs of the projected optical axis have a dichroic reflection angle of less than about 20 degrees.

6. The detector assembly of claim 5, wherein the reflected legs of the projected optical axis have a dichroic reflection angle of less than about 19 degrees.

7. The detector assembly of claim 6, wherein the reflected legs of the projected optical axis have a dichroic reflection angle of less than about 18 degrees.

8. The detector assembly of claim 1, wherein said dichroic filters are located in slots, and wherein each row of slots includes a plurality of evenly spaced slots.

9. The detector assembly of claim 1, wherein the optical alignment assembly comprises:
   a housing having a longitudinal axis and configured to receive an optical fiber;
   a collimating lens configured to collimate a beam of light emitted by the optical fiber;
   a rotatable housing member having a goniometric tilt;
   a beam reflecting element attached to the rotatable housing member; and
   an alignment system utilizing two adjustment mechanisms,
   wherein a first adjustment mechanism adjusts rotation of the rotatable housing member and a second adjustment mechanism adjusts the goniometric tilt of the rotatable housing member.

10. A detector assembly for analysis of light emitted, the detector assembly comprising:
    a dichroic filter array having a plurality of dichroic filters arranged in two rows in parallel, wherein said dichroic filters are located in slots, and wherein each row of slots includes a plurality of evenly spaced slots;
    a first optical alignment assembly having a longitudinal axis and configured to generate a first output beam having a first projected optical axis, wherein the first projected optical axis of the first output light beam, when reflected between the rows of dichroic filters, lies in a plane; and
    a second optical alignment assembly having a longitudinal axis and configured to generate a second output beam having a second projected optical axis wherein the second projected optical axis of the second output light beam, when reflected between the rows of dichroic filters, lies in the plane,
    wherein the first output beam enters the dichroic filter array at a first location and the second output beam enters the dichroic filter array at a second location, and
    wherein the first optical alignment assembly and the second output alignment assembly are positioned such that their respective longitudinal axes are each oriented orthogonal to the plane.

11. The detector assembly of claim 10 further comprising a third optical alignment assembly having a longitudinal axis and configured to generate a third output beam having a third projected optical axis, wherein the third output beam enters the dichroic filter array at a third location, and
    wherein the third projected optical axis of the third output light beam, when reflected between the rows of dichroic filters, lies in the plane, and
    wherein the third optical alignment assembly is positioned such that its respective longitudinal axis is oriented orthogonal to the plane.

12. The detector assembly of claim 10, wherein the dichroic filters are configured to split the output beam into a reflected leg and a transmitted leg.

13. The detector assembly of claim 10 further comprising a plurality of detector ports for receiving detectors therein, wherein said detectors receive a transmitted leg of the output beams.

14. The detector assembly of claim 10, wherein at least the second optical alignment assembly is configured to be removed from or repositioned on the detector assembly.

15. The detector assembly of claim 10, wherein the first optical alignment assembly comprises
    a housing configured to receive an optical fiber;
    a collimating lens configured to collimate a beam of light emitted by the optical fiber;
    a rotatable housing member having a goniometric tilt;
    a beam reflecting element attached to the rotatable housing member; and
    an alignment system utilizing two adjustment mechanisms;
    wherein a first adjustment mechanism adjusts rotation of the rotatable housing member and a second adjustment mechanism adjusts the goniometric tilt of the rotatable housing member.

16. An optical alignment assembly for introducing an output beam into an array of dichroic filters, the optical assembly comprising:
    a housing having a longitudinal axis and configured to receive an optical fiber;
    a collimating lens configured to collimate a beam of light emitted by the optical fiber;
    a rotatable housing member having a goniometric tilt;
    a beam reflecting element attached to the rotatable housing member; and
    an alignment system utilizing two adjustment mechanisms, wherein a first adjustment mechanism adjusts rotation of the rotatable housing member and a second adjustment mechanism adjusts the goniometric tilt of the rotatable housing member, wherein when the output beam is introduced into the array of dichroic filters, the output beam is reflected by the array of dichroic filters and lies in a plane that is orthogonal to the longitudinal axis of the housing.

17. The optical alignment assembly of claim 16, wherein the beam reflecting element is configured to reflect the collimated beam into the array of dichroic filters.

18. The optical alignment assembly of claim 16, wherein the first adjustment mechanism is independent from the second adjustment mechanism.

19. The optical alignment assembly of claim 16, wherein the beam reflecting element reflects light at a reflection point inside the beam reflecting element, and wherein the position of the reflection point remains substantially the same as the tilt of the rotatable housing member is adjusted.

20. The detector assembly of claim 16, wherein the beam reflecting element is a prism.

21. A method of demultiplexing a beam of light transmitted by an optical fiber, comprising:
 a) collimating the beam of light with a collimating lens;
 b) redirecting the beam of light with a beam reflecting element such that the beam of light enters a dichroic filter array having a plurality dichroic filters arranged in two rows in parallel, and is reflected within the dichroic filter array such that the reflected beam of light lies within a plane; and
 c) separating the beam of light into its component wavelengths by reflecting the beam of light off at least one of the dichroic filters, wherein the beam of light, prior to being redirected by the beam reflecting element, is approximately orthogonal to the plane of the reflected beam of light.

22. The method of claim 21, further comprising:
 d) filtering the beam of light with a bandpass filter.

23. The method of claim 21, wherein the beam of light is reflected off the at least one dichroic filter at an angle less than about 20 degrees.

24. The method of claim 21, step c) further comprising reflecting the beam of light off two or more of the dichroic filters, wherein the beam of light is alternately reflected between a dichroic filter located in the first row and a dichroic filter in the second row.

25. The method of claim 21, step b) further comprising goniometrically adjusting the angle at which the beam of light exits the beam reflecting element.

26. The detector assembly of claim 21, wherein the beam reflecting element is a prism.

* * * * *